US009763971B2

(12) United States Patent
Groenendijk et al.

(10) Patent No.: US 9,763,971 B2
(45) Date of Patent: *Sep. 19, 2017

(54) IMPROVING RECOGNITION (71) Applicant: N.V. Nutricia, Zoetermeer (NL)

(72) Inventors: Martine Groenendijk, Barendrecht (NL); Anke Bongers, Veenendaal (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/355,197

(22) PCT Filed: Oct. 30, 2012

(86) PCT No.: PCT/NL2012/050751
§ 371 (c)(1),
(2) Date: Apr. 29, 2014

(87) PCT Pub. No.: WO2013/066165
PCT Pub. Date: May 10, 2013

(65) Prior Publication Data
US 2014/0274938 A1 Sep. 18, 2014

(30) Foreign Application Priority Data
Oct. 31, 2011 (WO) ................ PCT/NL2011/050737

(51) Int. Cl.
| | |
|---|---|
| *A01N 43/04* | (2006.01) |
| *A61K 31/70* | (2006.01) |
| *A61K 31/7072* | (2006.01) |
| *A61K 45/06* | (2006.01) |
| *A61K 31/14* | (2006.01) |
| *A61K 31/202* | (2006.01) |
| *A61K 31/355* | (2006.01) |
| *A61K 31/375* | (2006.01) |
| *A61K 31/4415* | (2006.01) |
| *A61K 31/519* | (2006.01) |
| *A61K 31/683* | (2006.01) |
| *A61K 31/685* | (2006.01) |
| *A61K 31/7068* | (2006.01) |
| *A61K 31/714* | (2006.01) |
| *A61K 33/04* | (2006.01) |
| *A23L 5/00* | (2016.01) |
| *A23L 33/12* | (2016.01) |
| *A23L 33/13* | (2016.01) |
| *A61K 31/7064* | (2006.01) |
| *A61K 31/706* | (2006.01) |

(52) U.S. Cl.
CPC ............ *A61K 31/7072* (2013.01); *A23L 5/00* (2016.08); *A23L 33/12* (2016.08); *A23L 33/13* (2016.08); *A61K 31/14* (2013.01); *A61K 31/202* (2013.01); *A61K 31/355* (2013.01); *A61K 31/375* (2013.01); *A61K 31/4415* (2013.01); *A61K 31/519* (2013.01); *A61K 31/683* (2013.01); *A61K 31/685* (2013.01); *A61K 31/7068* (2013.01); *A61K 31/714* (2013.01); *A61K 33/04* (2013.01); *A61K 45/06* (2013.01); *A23V 2002/00* (2013.01); *A61K 31/706* (2013.01); *A61K 31/7064* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 5,470,838 | A | 11/1995 | Von Borstel et al. |
| 6,316,426 | B1 | 11/2001 | Von Borstel et al. |
| 8,282,335 | B2 | 10/2012 | Bark |
| 8,283,336 | B2 | 10/2012 | Groenendijk et al. |
| 8,361,989 | B2 | 1/2013 | Groenendijk et al. |
| 8,759,319 | B2 | 6/2014 | Hageman et al. |
| 8,791,089 | B2 | 7/2014 | Groenendijk et al. |

FOREIGN PATENT DOCUMENTS

| | | |
|---|---|---|
| WO | WO-2007/089703 A2 | 8/2007 |
| WO | WO-2009/002146 A1 | 12/2008 |
| WO | WO-2009/002148 A1 | 12/2008 |
| WO | WO-2009/002163 A1 | 12/2008 |
| WO | WO-2009/002164 A1 | 12/2008 |
| WO | WO-2009/002165 A1 | 12/2008 |
| WO | WO-2009/002166 A1 | 12/2008 |
| WO | WO-2009/057994 A1 | 5/2009 |
| WO | WO-2009/082203 A1 | 7/2009 |
| WO | WO-2011/011721 A2 | 1/2011 |

OTHER PUBLICATIONS

Rabin et al. Archives of Clinical Neuropsychology (2005), vol. 20, pp. 33-65.*
Westerberg et al. Neuropsychology (2006), 20(2): 193-205.*
Decision Science News (Sep. 27, 2006).*
Birenbaum et al. Applied Psychological Measurement (1987), 11(4): 385-95.*
Harrison, John et al., "A neuropsychological test battery for use in Alzheimer disease clinical trials", Archives of Neurology, vol. 64, No. 9, Sep. 2007, pp. 1323-1329.
International Search Report mailed Dec. 14, 2012 in PCT/NL2012/050753.
International Search Report mailed Feb. 20, 2013 in PCT/NL2012/050754.
International Search Report mailed Nov. 29, 2012 in PCT/NL2012/050751.
Lannfelt, et al. "Safety, efficacy, and biomarker findings of PBT2 in targeting Abeta as a modifying therapy for Alzheimer's disease: a (Continued)

*Primary Examiner* — Patrick Lewis
(74) *Attorney, Agent, or Firm* — Gilberto M. Villacorta; Sunit Talapatra; Foley & Lardner LLP (57) ABSTRACT

The invention relates to a composition for use in the treatment or prevention of recognition dysfunction, and/or for improving recognition, in a (prodromal) Alzheimer's patient, in particular in a drug-naive (prodromal) Alzheimer's patient, more particularly in a subject with a mini-mental state examination of 20-30.

21 Claims, 1 Drawing Sheet

(56) References Cited

OTHER PUBLICATIONS phase IIa, double-blind, randomised, placebo-controlled trial" The Lancet Neurology, 2008, vol. 7, Issue 9, pp. 779-786.

Scheltens et al., "Efficacy of a medical food in mild Alzheimer's disease: A randomized controlled trial", Alzheimer's & Dementia (2010), vol. 6, No. 1, pp. 1-10.

Snyder, Peter J. "Assessment of cognition in mild cognitive impairment: A comparative study", Alzheimer's & Dementia: The Journal of the Alzheimer's Association, vol. 7, No. 3, Sep. 2007, pp. 338-355.

Beers et al., "Section 1; Nutritional Disorders; Chapter 1, Nutrition: General Considerations," The Merck Manual of Diagnosis and Therapy, 17th Edition, Merck & Co., Whitehouse Station , N.J., 1999, pp. 1-23.

Debruin et al., "Combined uridine and choline administration improves cognitive deficits in spontaneously hypertensive rats", Neurobiology of Memory and Learning, Jul. 2003, vol. 80, No. 1, pp. 63-79.

* cited by examiner

IMPROVING RECOGNITION

CROSS-REFERENCE TO RELATED APPLICATIONS

This application is the National Phase of International Patent Application No. PCT/NL2012/050751, filed Oct. 30, 2012, published as WO 2013/066165, which claims priority to International Application No. PCT/NL2011/050737, filed Oct. 31, 2011. The contents of these applications are herein incorporated by reference in their entirety.

FIELD OF THE INVENTION

The invention relates to a composition for use in the treatment or prevention of recognition dysfunction, and/or for improving recognition, preferably in a (prodromal) Alzheimer's patient, in particular in a drug-naive (prodromal) Alzheimer's patient, more particularly in a subject with a mini-mental state examination of 20-30.

BACKGROUND OF THE INVENTION

Memory impairment is a serious shortcoming in many humans, particularly those suffering from Alzheimer's disease and/or elderly. Such impairments often have serious consequences, such as reduced quality of life, difficulties in performing the activities of daily living, behavioural problems, potentially resulting in hospitalization or institutionalization.

Several treatments have been suggested for the improvement of memory function in subjects. However, very few have been proven effective. Moreover, the administration of several nutritional ingredients has also been suggested.

WO 2009/002166A1 describes a composition comprising (a) uridine or uridine phosphate; and (b) DHA and/or EPA for improving delayed recall function in a subject with a MMSE of 24-26.

SUMMARY OF THE INVENTION

The present invention relates to a composition comprising:
a. one or more omega 3 fatty acids selected from the group consisting of docosahexaenoic acid (DHA), eicosapentaenoic acid (EPA), and docosapentaenoic acid (DPA); and
b. a uridine source selected from uridine, deoxyuridine, uridine phosphates, uracil, acylated uridine, and cytidine;
for improving recognition and/or for use in the treatment or prevention of impaired recognition function of a subject.

The invention can also be referred to as the use of a composition comprising (a) and (b) for the manufacture of a product for improving recognition and/or for use in the treatment or prevention of impaired recognition function of a subject, wherein (a) is one or more omega 3 fatty acids selected from the group consisting of docosahexaenoic acid (DHA), eicosapentaenoic acid (EPA), and docosapentaenoic acid (DPA); and (b) is a uridine source selected from uridine, deoxyuridine, uridine phosphates, uracil, acylated uridine, and cytidine.

The invention can also be referred to as the use of (a) and (b) for the manufacture of a composition for improving recognition and/or for use in the treatment or prevention of impaired recognition function of a subject, wherein (a) is one or more omega 3 fatty acids selected from the group consisting of docosahexaenoic acid (DHA), eicosapentaenoic acid (EPA), and docosapentaenoic acid (DPA); and (b) is a uridine source selected from uridine, deoxyuridine, uridine phosphates, uracil, acylated uridine, and cytidine.

Preferably, the composition comprises EPA and/or DHA, and a uridine source selected from uridine, deoxyuridine, uridine phosphates, uracil, acylated uridine, and cytidine.

More preferably, the composition comprises, per daily dose or preferably per 100 ml composition, at least 500 mg of DHA, preferably at least 600 mg of DHA, and at least 50 mg of uridine, preferably at least 100 mg of uridine. Even more preferably, the composition comprises, per daily dose or preferably per 100 ml composition, at least 500 mg of DHA, preferably at least 600 mg of DHA, and at least 50 mg of UMP, preferably at least 100 mg of UMP.

Preferably, the composition further comprises choline, or salts, or esters thereof. In particular, the composition comprises, per daily dose or preferably per 100 ml composition, 200-600 mg choline, more preferably 300-400 mg choline.

Preferably, the composition further comprises phospholipids.

Preferably, the composition further comprises vitamin E; in particular in the form of alpha-tocopherol.

Preferably, the composition further comprises selenium.

Preferably, the composition further comprises folic acid.

Preferably, the composition further comprises vitamin B12.

Preferably, the composition further comprises vitamin B6.

Particularly preferred, besides the omega 3 fatty acids and the uridine source, the composition further comprises one or more of the components/ingredients selected from the group consisting of phospholipids, vitamin E, vitamin C, selenium, vitamin B12, vitamin B6 and folic acid. Preferably, the composition comprises, per daily dose or preferably per 100 ml composition: 50-1000 mg phospholipids, 0.5-3 mg vitamin B6, 50-500 µg folic acid, and 1-30 µg vitamin B12, Preferably, the composition comprises, per daily dose or preferably per 100 ml composition, 20-60 mg vitamin E, preferably in alpha tocopherol form, and 60-100 mg vitamin C.

According to a preferred embodiment, the composition comprises, per daily dose or preferably per 100 ml composition:
100-500 mg, preferably 200-400 mg EPA,
1000-1500 mg, preferably 1100-1300 mg DHA,
50-600 mg, preferably 60-200 mg phospholipids,
200-600 mg, preferably 300-500 mg choline,
400-800 mg, preferably 500-700 mg UMP (uridine monophosphate),
20-60 mg, preferably 30-50 mg vitamin E (alpha-TE),
60-100 mg, preferably 70-90 mg vitamin C,
40-80 µg, preferably 50-70 µg selenium,
1-5 µg, preferably 2-4 µg vitamin B12,
0.5-3 mg, preferably 0.5-2 mg vitamin B6, and
200-600 µg, preferably 300-500 µg folic acid.

Preferably, the composition has, per daily dose or preferably per 100 ml composition, an energy content of 50-130 kcal, a protein content of 1-10 g, a lipids content of lipids 1-5 g, and a content of digestible carbohydrates of 4-20 g.

Preferably, the subject has one or more symptoms of Alzheimer's disease, mild cognitive impairment, age-associated memory impairment, multiple sclerosis, vascular dementia, frontotemporal dementia, semantic dementia or dementia with Lewy bodies. More preferably, the subject is a (prodromal) dementia and/or a (prodromal) Alzheimer patient. Even more preferably, the subject is a dementia and/or an Alzheimer patient. And even more preferably, the subject is an Alzheimer patient (i.e. has/suffers from Alzheimer's disease).

Preferably, the subject has a mini-mental state examination (MMSE) score of 20-30, in particular of 20-26, more particularly of 24-26.

Preferably, the subject is drug-naïve.

Preferably, the composition is enterally administered to the patient at least one time per day for a period of at least 12 weeks, preferably at least 13 weeks, more preferably at least 14, 15, 16, 17, 18, 19, 20, 21, 22, 23, or 24 weeks.

The present invention also relates to a method for improving recognition, or for treating or preventing impaired recognition function of a subject, comprising administering to said subject a composition comprising:

a. one or more omega 3 fatty acids selected from the group consisting of docosahexaenoic acid (DHA), eicosapentaenoic acid (EPA), and docosapentaenoic acid (DPA); and
b. a uridine source selected from uridine, deoxyuridine, uridine phosphates, uracil, acylated uridine, and cytidine.

Preferably, said subject is drug-naïve.

Preferably, in a method of the invention, the subject has a mini-mental state examination (MMSE) score of 20 or higher, in particular of 20-26, more particularly of 24-26.

In particular, the subject suffers from, or has one or more symptoms of Alzheimer's disease, mild cognitive impairment, age-associated memory impairment, multiple sclerosis, vascular dementia, frontotemporal dementia, semantic dementia or dementia with Lewy bodies.

Preferably, the method of the invention is a method of therapeutically treating or preventing the recognition dysfunction of a subject, in particular a subject having Alzheimer's disease, mild cognitive impairment, age-associated memory impairment, multiple sclerosis, vascular dementia, frontotemporal dementia, semantic dementia or dementia with Lewy bodies, said method comprising:

administering a composition comprising (a) one or more omega-3 fatty acids selected from the group consisting of docosahexaenoic acid (DHA), eicosapentaenoic acid (EPA), and docosapentaenoic acid (DPA); and (b) a uridine source selected from uridine, deoxyuridine, uridine phosphates, uracil, and acylated uridine, and comprising monitoring or assessing the subject by one or more of the tests of the following neurological tests:
RAVLT-recognition,
RBANS-recognition, and
CVLT-recognition.

The present inventors surprisingly found, through clinical study, that administration of a composition containing (a) docosahexaenoic acid (DHA) and/or eicosapentaenoic acid (EPA) and/or docosapentaenoic acid (DPA); and (b) uridine and/or uridine phosphate, showed a significant improvement of recognition function in an Alzheimer's patient, having a MMSE of 20 or higher (i.e. of 20-30). Compliance and tolerability were very high and side effects were relatively low. It was particularly surprising that the present clinical data showed an actual improvement in recognition memory function, more than just a reduction in the rate of decline in recognition memory function. The results of the clinical study are summarized in the examples section.

DETAILED DESCRIPTION OF THE INVENTION

The invention relates to a composition comprising:
a. docosahexaenoic acid (DHA), and/or eicosapentaenoic acid (EPA), and/or docosapentaenoic acid (DPA); and
b. a uridine source, selected from uridine, deoxyuridine, uridine phosphates, uracil, acylated uridine, and cytidine;
for use for improving recognition and/or for the treatment or prevention of impaired recognition function in a subject.

Subjects

Preferably, in the present invention, the subjects are drug-naïve subjects. In particular, the subjects have not been administered any drug for memory improvement and/or for Alzheimer's disease prior to the administration of a composition according to the prevent invention.

Preferably, the term "drug naïve" as used in the present invention refers to subjects who do not ingest one or more of cholinesterase inhibitors, N-methyl-D-aspartate (NMDA) antagonists and ginkgo biloba.

As a preferred embodiment, e.g. in the clinical study presented herein, it was found that the composition according to the invention is very effective in drug naïve subjects that do not use omega-3 fatty acid containing supplements; oily fish more than twice a week; more than 200% RDI (Reference Daily Intake) of vitamins B, C and/or E; high energy and high protein nutritional supplements/medical foods; other investigational products; donepezil; rivastigmine; galantamine; and/or memantine.

The subject is preferably a human, preferably an elderly human, preferably at least 50 years of age.

Preferably, in the present invention, the subjects have a mini-mental state examination (MMSE) of 20-30, more preferably of 20-26, even more preferably of 24, 25 or 26.

The mini-mental state examination (MMSE) is a brief 30-point questionnaire test that is used to assess cognition. In the time span of about 10 minutes it samples various functions including memory and orientation. The MMSE test includes simple questions and problems in a number of areas: the time and place of the test, repeating lists of words, language use and comprehension, and basic motor skills.

A score of 27 or higher (out of 30) is interpreted generally as effectively normal, but does not allow to conclude that the subject is not suffering from (or having one or more symptoms of) Alzheimer's disease, mild cognitive impairment, age-associated memory impairment, multiple sclerosis, vascular dementia, frontotemporal dementia, semantic dementia or dementia with Lewy bodies.

A score of 20-26 indicates mild/early dementia; 10-19 moderate dementia, and below 10 severe dementia.

The MMSE is a standardized test. Copyrights prevent the inventors from including a copy of the questionnaire into the specification, but it is readily accessible on the internet and available through copyright owner Psychological Assessment Resources (PAR). It is first introduced by Folstein et al.

(Psych Res 12:189, 1975), and is widely used with small modifications to assess cognition.

Preferably, the subjects as treated in the present invention have a mini-mental state examination score of 20-30, preferably 20-26, even more preferably of 24, 25 or 26.

Preferably, the subjects have a MMSE score between 20 and 30, preferably 20-26, even more preferably of 24, 25 or 26 and do not receive/take medication for memory impairment and/or for Alzheimer's disease, and even more preferably are drug naïve subjects. The treatment of this subgroup is of particular interest as in these subjects the balance between side effects and benefits of pharmaceutical intervention is still negative. Providing nutritional therapy to these subjects is desired because of the relative lack of negative side effects. For these drug naïve subjects, it is particularly important to develop a therapy which delays the point in time where pharmaceutical drugs with negative side effects have to be administered.

Alternatively, the subjects have a MMSE score between 20 and 30, preferably 20-26, even more preferably of 24, 25 or 26 and have (or suffer from) Alzheimer's disease, mild cognitive impairment (MCI), age-associated memory impairment (AAMI), multiple sclerosis, vascular dementia, frontotemporal dementia, semantic dementia or dementia with Lewy bodies, more particularly have (or suffer from) Alzheimer's disease.

Recognition improvement through nutritional therapy is particularly desired in subjects with a mild/early form of Alzheimer's Disease. Pharmaceutical intervention with drugs having negative side effects could be reduced or even postponed if significant improvements are observed.

More preferably, the subjects have a MMSE score between 20 and 30, preferably 20-26, even more preferably of 24, 25 or 26, are drug naïve, and have (or suffer from) Alzheimer's disease, mild cognitive impairment (MCI), age-associated memory impairment (AAMI), multiple sclerosis, vascular dementia, frontotemporal dementia, semantic dementia or dementia with Lewy bodies, more particularly have (or suffer from) Alzheimer's disease.

Even more preferably, the subjects as treated in the present invention have a MMSE score of 20-26, are drug naïve, and suffer from Alzheimer's disease.

Prodromal dementia and/or Alzheimer patients are defined to be persons that score positively on at least one, preferably at least two, more preferably at least three of the following criteria:
- a level of more than 350 ng Total-tau per liter cerebrospinal fluid (CSF);
- a weight ratio of abeta-42/Phospho-tau-181 of less than 6.5 in CSF;
- presence of medial temporal lobe (MTL) atrophy, existing of volume loss of hippocampus, entorhinal cortex, or amygdala evidenced on Magnetic Resonance Imaging (MRI) with either qualitative ratings using visual scoring (referenced to well characterised population with age norms) or quantitative volumetry of regions of interest (referenced to well characterized population with age norms)
- presence of fronto-temporal lobe (FTL) atrophy evidenced on MRI with qualitative ratings or quantitative volumetry;
- a level of more than 25 pg F2-iso-prostane (F2-IsoP, isoprostane 8,12-iso-iPF2alpha-VI) per mL CSF.

Further explanations of the significance of concentrations of T-tau, P-tau181, Abeta42 and F2-Isoprostane in CSF for future development of Alzheimer's disease can be found in: Hansson O, Zetterberg H, Buchhave P, Londos E, Blennow K, Minthon L (2006) Association between CSF biomarkers and incipient Alzheimer's disease in patients with mild cognitive impairment: a follow-up study. Lancet Neurol 5:228-234; and in Pratico D, Clark C M, Liun F, Lee V Y M, Trojanowski J Q (2002) Increase in brain oxidative stress in mild cognitive impairment: a possible predictor of Alzheimer disease. Arch Neurol 59:972-976.

In a preferred embodiment, the identification of prodromal dementia and/or Alzheimer patients comprises at least the first two criteria (total tau and ratio abeta-42/P-tau-181). More preferably, one of the three other criteria (MTL atrophy, FTL atrophy, F2-IsoP) is also applied.

In addition to or instead of one or more of the above criteria, the following can be advantageously used:
- reduced glucose metabolism in bilateral temporal parietal areas of the brain, as is detectable by Positron Emission Tomography (PET);
- reduced glucose metabolism in the posterior cingulate cortex, as is detectable by PET;
- impaired blood flow in the brain as measurable by applying Single-Photon Emission Computed Tomography (SPECT), for example by applying the radioisotope 99mTc-HMPAO);
- impaired glucose metabolism in the brain as measurable by applying SPECT;
- abnormalities in the histology of the medial or inferior temporal lobes as can be determined by MRI or in the rate of glucose utilisation;
- abnormalities in histology or glucose utilization in the temporal parietal cortex or posterior cingulate cortex.

Abnormalities in the condition of the brain or parts thereof can be established by either taking the person's own condition under healthy circumstances as a reference, or, when this is not available, by taking the average condition of a representative group (so matched for e.g. age) as a reference. The latter will occur most frequently. By comparison of the patient's condition with the reference situation and the average situation when the pathological condition would have been developed to its full extent, the clinician is capable of recognizing a prodromal phase. In particular an intermediate situation wherein the patient demonstrates a deviation of x % from the value of a healthy individual in the direction of the pathological conditions is for the purpose of this invention considered to be a prodromal patient. The value of x for the determination of blood flow and glucose metabolism is 20% when determined under standardised conditions in terms of feeding and exercise.

Recognition

It was particularly found that in Alzheimer's patients, in particular drug-naive Alzheimer's patients, the recognition function was improved.

The present invention relates to a composition for use for (i) improving recognition and/or (ii) treating and/or preventing impaired recognition function.

Alternatively, the present invention provides a method for (i) the improvement of recognition and/or (ii) treatment and/or prevention of impaired recognition function in a subject in need thereof, said method comprising the administration of the present composition to said subject. Particularly, the present invention relates to the treatment or prevention of an impaired recognition function.

It was found that the recognition function actually improved when the present composition was administered to the subject.

The recognition function of a human subject can suitably be determined using one or more of the following tests:

RAVLT-recognition, "Repeatable Battery for the Assessment of Neuropsychological Status", or "California Verbal Learning Test".

Preferably, in the context of the present invention, the term "recognition" and the term "recognition memory" are synonymous, and refer to a subcategory of memory. Preferably, both terms refer to the ability to recognize previously encountered events, objects, or people; and when the previously-experienced event, person, or thing is re-experienced, this environmental content is matched to stored memory representations, eliciting matching signals. Recognition can be regarded as involving both recollection (also referred to as remembering, regarded as a slow, controlled search process) and familiarity (also referred to as knowing, and considered as a fast, automatic process). Recognition (memory) is not confined to the visual domain, and can involve each of the five traditional sensory modalities (i.e. sight, hearing, touch, smell, and taste). Although most neuroscientific research has focused on visual recognition, there have also been studies (known in the art) related to audition (hearing), olfaction (smell), gustation (taste), and taction (touch). Preferably, a composition according to the invention is for use for improving audition (or hearing, or verbal) recognition, and/or visual recognition, and more preferably is for use for improving both verbal and visual recognition.

In these subjects administered the composition according to the invention, the (immediate and/or delayed) recall function was improved also.

Immediate recall function can be measured e.g. using the WMS-VPA immediate test.

Delayed recall function can be measured by a prose recall task after a delay set in the protocol. Hence, the present composition can also advantageously help the subject(s) in improving the recall function. Hence, in a preferred embodiment the invention provides a composition or a method for improving both recall and recognition functions, and/or the treatment and/or prevention of both impaired recall function and impaired recognition function.

The Tests

The neuropsychological tests are specifically designed tasks used, e.g. in the clinical trial as described in the example section, to measure a psychological function known to be linked to a particular brain structure or pathway. Tests are used for research into brain function and in a clinical setting for the diagnosis of deficits. They usually involve the systematic administration of clearly defined procedures in a formal environment, and they form a core component of the process of conducting neuropsychological assessment, along with personal, interpersonal and contextual factors (source: http://en.wikipedia.org/wiki/Neuropsychological_test).

Rey Auditory Verbal Learning Test (RAVLT) for recall and recognition.

The Rey Auditory verbal Learning Test is a measure of both immediate and delayed episodic verbal learning and memory. The test is 'episodic' in that the reading of the word list represents an episode in the subject's memory.

The RAVLT is useful in evaluating verbal learning and memory, including proactive inhibition, retroactive inhibition, retention, encoding versus retrieval, and subjective organization. Because the test is brief, straightforward, easy to understand, and appropriate for children, adolescents, and adults ages 7-89 years, it has gained widespread acceptance (source: http://www.annarbor.co.uk/index.php?mainpage=index&cPath=249_303)

For instance, in the immediate recall component (RAVLT-immediate) words are read to the subjects and they are required to recall them as best as they are able after the test administrator has completed reading the list. This first words list (List A), of e.g. 15 words, is read several times, e.g. a total of 3, or 4 or 5 times, and word(s) recall for each of the trials is recorded. It is possible to determine the rate of learning by observing whether there is improved recall with repeated exposure to the words list.

After the trials of List A, a second list (List B), of e.g. 15 words, is read to the subjects. Recall for List B is recorded and then the subjects are again asked to recall words from List A. The administration of List B is designed to interfere with recall of List A to make recall more difficult. For the delayed recall component (RAVLT-delayed), a delay interval, e.g. 10 to 30 minutes, after this last stage of the test, the subjects are asked to recall the words from List A.

In the final stage of the test, corresponding to the recognition component (RAVLT-recognition), the subjects are asked to identify List A words from a written list of words. The list is comprised of the original List A words intermingled with new 'distractor' words, e.g. the 15 words of list A intermingled with 15 new 'distractor' words. Performance on recognition memory tasks typically exceeds that for word recall and so is useful addition in studies of individuals whose memory maybe impaired.

Verbal Paired Associates (VPA) test from the Wechsler Memory Scale-Revised (WMS-R).

Paired associative learning tests require the subject to associate two items in memory. Some tasks that feature this paradigm require the subjects to associate colours with shapes or objects with spatial locations.

The VPA requires the subjects to associate two words in memory. Several pairs of words (e.g. 8 pairs of words) are read out loud, some (e.g. 4) 'easy' pairs that are semantically related, such as 'BABY-CRIES' or 'METAL-IRON' and some (e.g. 4) 'Hard' pairs that require an association to be made between semantically unrelated word pairs, such as 'CRUSH-DARK'. The word pairs are presented auditorily and then immediate recall is tested by having the test administrator say the first word of each pair as a cue. The subjects must in response to the cue say the paired word. All subjects undergo several trials (e.g. 3 trials) of all pairings and are awarded one point for each correct response (WMS-VPA immediate).

This test includes a delayed recall condition, e.g. 1 to 30 minutes, after the immediate recall test (WMS-VPA delayed) and in an attempt to encourage high levels of delayed recall, study participants who fail to score the highest score (e.g. 8 on trial 3) of immediate recall then undergo further trials (e.g. a 4th, 5th and, if necessary, 6th trial). If perfect performance is achieved, e.g. on trial 3 or any successive trial, the immediate recall component is ended. If not, further trials are administered (e.g. to a maximum of six trials). At delayed recall all cue words (e.g. 8) are presented and the subjects are requested to provide the correct paired word Immediate recall yields a score comprised between 0 and pairs number x trials (e.g. between 0 and 8 pairs×3 trials=24) and delayed recall a score comprised between 0 and the number of pairs (e.g. 0-8). In both cases higher scores indicate superior performance.

Repeatable Battery for the Assessment of Neuropsychological Status (RBANS), as described e.g. in the RBANS manual by Randolf 1998, can be used to score the recognition performance (RBANS-recognition), and thereby assess or monitor the recognition function.

California Verbal Learning Test (CVLT), see e.g. in Delis, D. C., Kramer, J. H., Kaplan, E., & Ober, B. A. (2000), can be used to score the recognition performance (CVLT-recognition), and thereby assess or monitor the recognition function.

All these different tests can be adapted, as well known in the art.

Uridine

Preferably, the composition to be administered according to the present invention comprises a source of uridine selected from uridine, deoxyuridine, uridine phosphates, uracil, acylated uridine, and cytidine.

Dietary cytidine, being converted into uridine in humans, can be regarded as a source of uridine in the context of the present invention. Therefore, the composition to be administered according to the present invention can comprise, as a source of uridine, cytidine, deoxycytidine, cytidine phosphates, cytosine and/or acylated cytidine.

Preferably, the present composition comprises uridine and/or uridine phosphate, more preferably comprises uridine phosphate.

In particular, the present composition comprises one or more uridine phosphates selected from uridine monophosphate (UMP), uridine diphosphate (UDP) and uridine triphosphate (UTP), and more preferably UMP.

Most preferably the present composition comprises UMP. Preferably at least 50 wt. % of the uridine in the present composition is provided by UMP, more preferably at least 75 wt. %, most preferably at least 95 wt. %. The present method preferably comprises the administration of uridine (the cumulative amount of uridine, deoxyuridine, uridine phosphates, uracil and acylated uridine derivatives) in an amount of 0.08-3 g per day, preferably 0.1-2 g per day, more preferably 0.2-1 g per day. The present method preferably comprises the administration of a composition comprising uridine in an amount of 0.08-3 g UMP per 100 ml liquid product, preferably 0.1-2 g UMP per 100 ml liquid product, more preferably 0.2-1 g per 100 ml liquid product. Preferably 1-37.5 mg UMP per kilogram body weight is administered per day. The required dosages of the equivalents on a weight base can be calculated from the dose for UMP by taking equimolar amounts using the molecular weight of the equivalent and of UMP, the latter being 324 Dalton.

Docosahexaenoic Acid, Eicosapentaenoic Acid and/or Docosapentaenoic Acid.

The present composition preferably comprises at least docosahexaenoic acid (22:6 ω-3; DHA) and/or eicosapentaenoic acid (20:5 ω-3; EPA) and/or docosapentaenoic acid (22:5 ω-3; DPA), preferably DHA and/or EPA, more preferably DHA and EPA.

The DHA, EPA and/or DPA are preferably provided as triglycerides, diglycerides, monoglycerides, free fatty acids or their salts or esters, phospholipids, lysophospholipids, glycerol ethers, lipoproteins, ceramides, glycolipids or combinations thereof. More preferably, the present composition comprises at least DHA in triglyceride form.

Preferably, the present composition comprises DHA and EPA in sufficient amount for the administration of 400-5000 mg (DHA+EPA) per day, more preferably 500-3000 mg per day, most preferably 1000-2500 mg per day. The proportion of (DHA+EPA) of the total fatty acids present in the composition is preferably 5-50 wt. %, more preferably 10-45 wt. %, most preferably 15-40 wt. %. More preferably, the present composition comprises DHA in sufficient amount for the administration of DHA in an amount of 300-4000 mg per day, more preferably 500-2500 mg per day.

The present composition preferably contains a very low amount of arachidonic acid (AA). Preferably the weight ratio DHA/AA in the present composition is at least 5, preferably at least 10, more preferably at least 15, preferably up to e.g. 30 or even up to 60.

The present method preferably comprises the administration of a composition comprising less than 5 wt. % arachidonic acid based on total fatty acids, more preferably below 2.5 wt. %, e.g. down to 0.5 wt %.

The ratio omega-6/omega-3 fatty acids in the present product is preferably below 0.5, more preferably below 0.2, e.g. down to 0.05 or to 0.01. The ratio ω-6/ω-3 fatty acids (C 20 and higher) in the present product is preferably below 0.3, more preferably below 0.15, e.g. down to 0.06 or to 0.03.

An amount per day as described herein means an amount in a daily dosage unit provided by the composition of the invention. Such a daily dosage unit may be a single dosage, but it may also be divided over two or three, or even more daily servings. If the composition, as according to a preferred embodiment, is intended for administration as a single unit, the amounts per day as described herein, are preferably the amounts present in the (preferably packaged) composition unit.

Treatment preferably involves administration once, twice or three times per day, more preferably once per day for a period of at least 3 weeks, preferably for a period of at least 12 weeks, more preferably for a period of at least 13 weeks, more preferably for a period of at least 14, 15, 16, 17, 18, 19, 20, 21, 22, or 23 weeks, and even more preferably for a period of at least 24 weeks.

The present composition preferably comprises 1-40 wt. % DHA based on total fatty acids, preferably 3-36 wt. % DHA based on total fatty acids, more preferably 10-30 wt. % DHA based on total fatty acids. The present composition preferably comprises 0.5-20 wt. % EPA based on total fatty acids, preferably 2-10 wt. % EPA based on total fatty acids, more preferably 5-10 wt. % EPA based on total fatty acids. The above-mentioned amounts take into account and optimise several aspects, including taste (e.g. too high LCP levels reduce taste, resulting in a reduced compliance).

The present composition preferably contains at least one oil selected from fish oil, algae oil and eggs lipids. Preferably the present composition contains fish oil comprising DHA and EPA.

Saturated and Monounsaturated Fatty Acids

The present composition preferably comprises saturated and/or mono-unsaturated fatty acids. The amount of saturated fatty acids is preferably 6-60 wt. % based on total fatty acids, preferably 12-40 wt. %, more preferably 20-40 wt. % based on total fatty acids. In particular the amount of C14:0 (myristic acid)+C16:0 (palmitic acid) is preferably 5-50 wt. %, preferably 8-36 wt. %, more preferably 15-30 wt. %, based on total fatty acids. The total amount of monounsaturated fatty acids, such as oleic acid and palmitoleic acid, is preferably between 5 and 40 wt. %, more preferably between 15 and 30 wt. %. A composition with these preferred amounts was found to be very effective.

Phospholipids

Preferably, the present composition preferably comprises phospholipids, preferably 0.1-50 wt. % phospholipids based on total weight of lipids, more preferably 0.5-20 wt. %, more preferably between 1 and 10% wt. %, most preferably between 1 and 5 wt. % based on total weight of lipids. The total amount of lipids is preferably between 10 and 30 wt. % on dry matter, and/or between 2 and 10 g lipid per 100 ml for a liquid composition. The composition preferably comprises between 0.01 and 1 gram lecithin per 100 ml, more preferably between 0.05 and 0.5 gram lecithin per 100 ml. A composition with these preferred amounts was found to be very effective.

Choline

Preferably the present composition contains choline and/or phosphatidylcholine. The present method preferably comprises the administration of more than 50 mg choline per day, preferably 80-2000 mg choline per day, more preferably 120-1000 mg choline per day, most preferably 150-600 mg choline per day. The present composition preferably comprises 50 mg to 3 gram choline per 100 ml of the liquid formula, preferably 200 mg-1000 mg choline/100 ml.

Vitamins

The composition may advantageously contain vitamins, preferably vitamin C, vitamin E and B vitamins, more preferably vitamin C, vitamin E, vitamin B6, vitamin B12 and folic acid. Advantageously, vitamin B12 and folate are included. The present composition preferably comprises 50-1000 µg folic acid, more preferably 150-750 µg, most preferably 200-500 µg folic acid, per 100 ml liquid product. The present method preferably comprises the administration of 50-1000 µg folic acid per day, more preferably 150-750 µg, most preferably 200-500 µg folic acid per day. The present composition preferably comprises 0.5-15 µg vitamin B12, more preferably 1-10 µg, most preferably 1.5-5 µg vitamin B12, per 100 ml liquid product. The present method preferably comprises the administration 0.5-15 µg vitamin B12 per day, more preferably 1-10 µg, most preferably 1.5-5 µg vitamin B12 per day.

Advantageously, the composition according to the invention comprises 0.5-3 mg, preferably 0.5-2 mg vitamin B6, per 100 ml liquid product.

Preferably, vitamin B6, vitamin B12 and folate are included.

Product

Preferably, a composition according to the invention comprises:
one or more omega 3 fatty acids selected from the group consisting of docosahexaenoic acid (DHA), eicosapentaenoic acid (EPA), and docosapentaenoic acid (DPA); and
a uridine source selected from uridine, deoxyuridine, uridine phosphates, uracil, acylated uridine, and cytidine.

Preferably the composition further comprises choline.

Preferably the composition further comprises one or more of: phospholipids, vitamin E, vitamin C, selenium, vitamin B12, vitamin B6 and folic acid.

More preferably the composition comprises DHA, EPA, a uridine source (preferably UMP), phospholipids, choline, vitamin E, vitamin C, selenium, vitamin B12, vitamin B6 and folic acid.

A preferred composition according to the invention comprises, per daily dose or per 100 ml composition:
100-500 mg, preferably 200-400 mg EPA,
900-1500 mg, preferably 950-1300 mg DHA,
50-600 mg, preferably 60-200 mg phospholipids,
200-600 mg, preferably 300-500 mg choline,
400-800 mg, preferably 500-700 mg UMP (uridine monophosphate),
20-60 mg, preferably 30-50 mg vitamin E (alpha-TE),
60-100 mg, preferably 60-90 mg vitamin C,
40-80 µg, preferably 45-65 µg selenium,
1-5 µg, preferably 2-4 µg vitamin B12,
0.5-3 mg, preferably 0.5-2 mg vitamin B6, and
200-600 µg, preferably 300-500 µg folic acid.

More preferred, a composition according to the invention comprises per 100 ml composition:
100-500 mg, preferably 200-400 mg EPA,
900-1500 mg, preferably 950-1300 mg DHA,
50-600 mg, preferably 60-200 mg phospholipids,
200-600 mg, preferably 300-500 mg choline,
400-800 mg, preferably 500-700 mg UMP (uridine monophosphate),
20-60 mg, preferably 30-50 mg vitamin E (alpha-TE),
60-100 mg, preferably 60-90 mg vitamin C,
40-80 µg, preferably 45-65 µg selenium,
1-5 µg, preferably 2-4 µg vitamin B12,
0.5-3 mg, preferably 0.5-2 mg vitamin B6, and
200-600 µg, preferably 300-500 µg folic acid.

The present composition can be a ready-to-use liquid, solid, or semi-liquid product. Preferably, the composition is liquid, more preferably ready-to-use liquid.

The present composition is preferably enterally administered, more preferably orally. Most preferably the present composition is administered through a straw. When it is a ready-to-use liquid, the daily liquid amount is preferably between 75 and 200 ml per day or per unit, most preferably between 90 and 150 ml/day.

The subjects that can benefit from the method and composition of the invention often experience problems with eating. Their sensory capabilities and/or control of muscles can become imparted, as well as in some instances their ambition to apply proper eating habits. Swallowing and/or mastication may be problematic. Hence, the present composition is preferably provided in the form of a drink capable of being ingested through a straw.

The composition according to the invention preferably has a low viscosity, preferably a viscosity between 1 and 2000 mPa·s measured at a shear rate of 100 sec$^{-1}$ at 20° C., more preferably a viscosity between 1 and 100 mPa·s measured at a shear rate of 100 sec$^{-1}$ at 20° C. More preferably, the present composition is provided in the form of a drink capable of being ingested through a straw which makes the product even easier to ingest and improves compliance. In a preferred embodiment the present composition has a viscosity of 1-80 mPas at a shear rate of 100 per sec at 20° C., more preferably of 1-40 mPas at a shear rate of 100 per sec at 20° C. These viscosity measurements may for instance be performed using plate and cone geometry.

To be optimally accepted by the subject, the present composition preferably has an osmolality of 300 to 800 mOsm/kg. However, the energy density of the product is preferably not so high that it interferes with normal eating habits. When in liquid form, the present product preferably contains between 0.2 and 3 kcal/ml, more preferably between 0.5 and 2, between 0.7 and 1.5 kcal/ml.

Advantageously the present composition contains digestible carbohydrates. The present composition preferably contains between 1 and 50 gram digestible carbohydrates per 100 ml of a liquid product, more preferably between 5 and 30 grams per 100 ml, more preferably 10-30 grams carbohydrates per 100 ml. The total amount of digestible carbohydrates is preferably between 25 and 80 wt. % on dry matter, preferably 40-80 wt. % based on dry matter.

The present composition may further comprise protein, preferably 0.5-10 g protein per 100 ml, more preferably 1-6 gram protein per 100 ml, most preferably 2-6 gram protein/100 ml. Preferably the present composition contain at least 80 wt. % milk derived protein (e.g. whey and/or casein) based on total protein. Proteins enable the manufacturing of palatable products, especially for frail elderly.

EXAMPLES

Example 1

Packaged composition for the comprising per 125 ml:
Energy 125 kcal; Protein 3.9 g; Carbohydrate 16.5 g; Fat 4.9 g.
Fat includes 1.5 g DHA+EPA, and 106 mg phospholipids (soy lecithin); Choline 400 mg; UMP (uridine monophosphate) 625 mg; Vitamin E 40 mg α-TE; Vitamin C 80 mg; Selenium 60 µg; Vitamin B12 3 µg; Vitamin B6 1 mg; Folic acid 400 µg.
Minerals and trace elements: Sodium 125 mg; Potassium 187.5 mg; Chloride 156.3 mg; Calcium 100 mg; Phosphorus 87.5 mg; Magnesium 25 mg; Iron 2 mg; Zinc 1.5 mg; Copper 225 µg; Manganese 0.41 mg; Molybdenum 12.5 µg; Chromium 8.4 µg; Iodine 16.3 µg. Vitamins: Vit. A 200 µg-RE; vit. D3 0.9 µg; vit. K 6.6 µg; Thiamin (B1) 0.19 mg; Riboflavin (B2) 0.2 mg; Niacin (B3) 2.25 mg-NE; Pantothenic acid (B5) 0.66 mg; Biotin 5 µg.

Example 2

Clinical Study.

A proof-of-concept study in drug-naïve patients with mild AD (MMSE 20-26) showed that a composition according to the invention (in particular the composition described in example 1) taken once per day was safe and improved delayed recall function of a subject after 12 weeks, the co-primary endpoint of the study (see Scheltens et al., "Efficacy of a medical food in mild Alzheimer's disease: A randomized controlled trial" Alzheimer's & Dementia 6 (2010), 1-10.).

The present study was designed to confirm the effect of the composition on memory in drug-naïve patients with mild AD, and also to extend the investigation through a longer intervention period of 24 weeks and through utilization of the whole memory domain z-score of a Neuropsychological Test Battery (NTB).

The present study was designed to investigate the effect of the composition on memory performance during 24 weeks intervention in drug-naïve patients with mild AD. Secondary objectives were to investigate safety and tolerance of the intervention, and to assess the effects on global cognition, functional abilities, and electroencephalography (EEG).

Material and Methods

The present study was a randomized, controlled, double-blind study, conducted at 27 study centers in six European countries (the Netherlands, Germany, France, Belgium, Italy and Spain). Drug-naïve patients with mild AD (MMSE scores≥20) and diagnosis of probable AD according to the NINCDS-ADRDA criteria, were randomly assigned (1:1) to the composition of example 1, or an iso-caloric control product. The duration of intervention was 24 weeks.

Compared to the composition of example 1, the control product lacked the following constituents: EPA, DHA, phospholipids, choline, UMP, vitamin E (alpha-TE), vitamin C, selenium, vitamin B12, vitamin B6 and folic acid.

The memory domain score of a Neuropsychological Test Battery (NTB) was the primary outcome parameter. This memory composite score was derived from the Rey Auditory Verbal Learning Test (RAVLT: immediate recall, delayed recall and recognition performance) and the Wechsler Memory Scale (WMS) verbal paired associates test (immediate and delayed recall).

Secondary outcomes resulting from the NTB were the executive function domain, total composite score and individual item scores. The other NTB items were WMS Digit Span, Trail Making Tests part A and B, Category Fluency, Controlled Word Association Test, the ADAS-cog orientation task and the Letter Digit Substitution Test. Main study parameters were assessed at baseline, week 12 and week 24. For the statistical analysis of the data, a repeated measures mixed model was used. The trial was registered with the ICMJE compliant www.trialregister.nl (NTR1975).

Results

A total of 259 drug-naïve subjects were randomized (2.6% screen failures). In the overall study population no differences in baseline characteristics were noted between the study groups. The mean age was 73.8 (±7.7) years, the mean screening MMSE was 25.0 (±2.8) and 51% were male. A pre-specified blinded interim analysis was conducted to check whether the calculated sample size was adequate and that no safety concerns had arisen, and the independent Data Monitoring Committee recommended continuation of the trial without modification. From the 259 subjects randomized, 238 subjects (91.9%) completed the study. Five subjects did not complete the study because of a (serious) adverse event ((S)AE); 3 in the group having received the composition and 2 in the control group, and no differences between study groups were noted in the occurrence of (S)AEs. No clinically relevant differences in blood safety parameters were noted. The average compliance during 24 weeks was very high at 97% and not different between the groups. High compliance was confirmed by marked and significant changes in (nutritional) biomarkers of compliance, e.g. docosahexaenoic acid in erythrocyte membranes and plasma homocysteine.

During 24 weeks, the composition according to the invention significantly improved the primary endpoint memory performance (composite memory domain z-score resulting from the NTB) compared to control product (repeated measures mixed model, p=0.025). The significant effect on memory performance was confirmed by individual tasks of the NTB memory domain.

Figure 1:
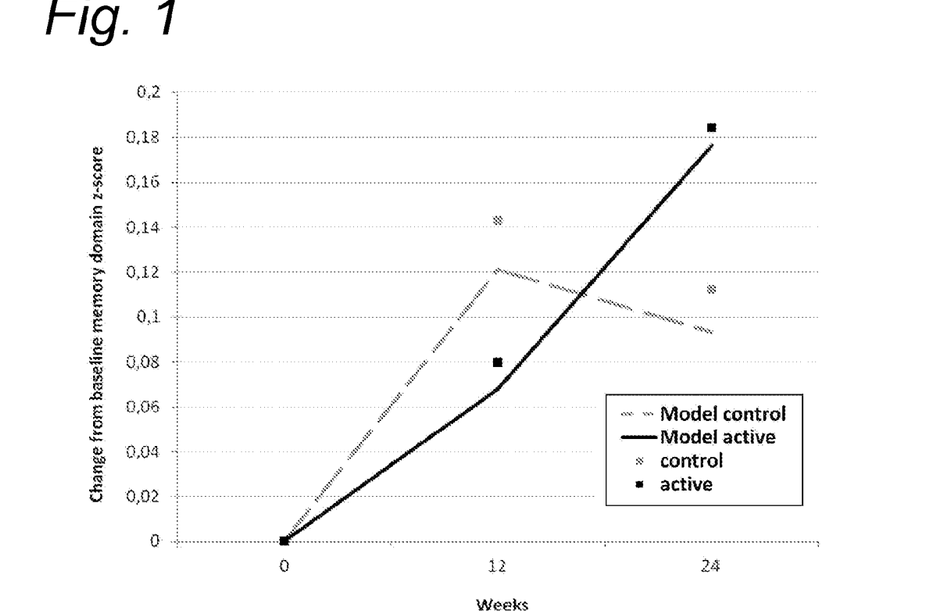
FIG. 1 represents the effect of a composition according to the invention on memory. The "Raw means: Active", showing a change from baseline memory domain z-score of 0.18 after 24 weeks, compared to the "Raw means: Control", with a change from baseline memory domain z-score of about 0.09 after 24 weeks, attests of the improvement effect on memory (p=0.032).
Figure 2:
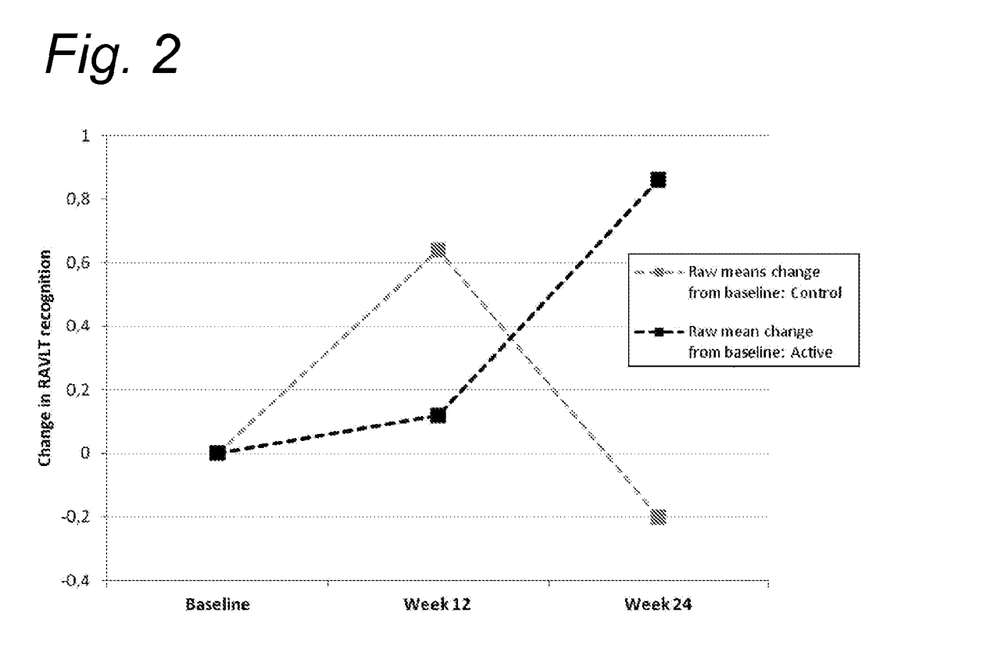
FIG. 2 represents the effect of a composition according to the invention on recognition. The "Raw means change from baseline: Active", showing a change in RAVLT-recognition of about 0.9 after 24 weeks, compared to the "Raw mean change from baseline: Control", with a negative change of about −0.2 after 24 weeks, attests of a very significant improvement effect on recognition (p=0.010).

Within the NTB memory domain, the results obtained for recognition (RAVLT-recognition score) are particularly significant (see FIG. 2). During 24 weeks, the composition according to the invention significantly improved the recognition performance compared to the control product (repeated measures mixed model, p=0.010).

The invention claimed is:

1. A method for improving recognition and/or treating impaired recognition function of a subject, said method comprising:
   (i) administering to said subject a composition comprising:
      (a) one or more omega 3 fatty acids selected from the group consisting of docosahexaenoic acid (DHA), eicosapentaenoic acid (EPA), and docosapentaenoic acid (DPA); and
      (b) a uridine source selected from uridine, deoxyuridine, uridine phosphates, uracil, acylated uridine, and cytidine;
   (ii) administering to said subject a recognition test, wherein the administration improves recognition and/or treats impaired recognition function of the subject compared to a subject not receiving the composition.

2. The method according to claim 1, wherein said subject has one or more symptoms of Alzheimer's disease, mild cognitive impairment, age-associated memory impairment, multiple sclerosis, vascular dementia, frontotemporal dementia, semantic dementia or dementia with Lewy bodies.

3. The method according to claim 1, wherein said subject is a prodromal dementia and/or a prodromal Alzheimer patient.

4. The method according to claim 1, wherein the composition comprises, per 100 ml composition, at least 500 mg of DHA and at least 50 mg of uridine.

5. The method according to claim 4, wherein the composition comprises, per 100 ml composition, at least 600 mg of DHA and at least 100 mg of uridine.

6. The method according to claim 1, wherein the composition further comprises choline, or salts, or esters thereof.

7. The method according to claim 6, wherein the composition comprises 200-600 mg choline per 100 ml composition.

8. The method according to claim 7, wherein the composition comprises 300-400 mg choline per 100 ml composition.

9. The method according to claim 1, wherein the composition further comprises one or more ingredients selected from the group consisting of phospholipids, vitamin E, vitamin C, selenium, vitamin B12, vitamin B6 and folic acid.

10. The method according to claim 9, wherein the composition comprises, per 100 ml composition:
 (a) 50-1000 mg phospholipids,
 (b) 0.5-3 mg vitamin B6,
 (c) 50-500 µg folic acid, and
 (d) 1-30 µg vitamin B12.

11. The method according to claim 10, wherein the composition comprises, per 100 ml composition, 20-60 mg vitamin E and 60-100 mg vitamin C.

12. The method according to claim 11, wherein the vitamin E is in alpha tocopherol form.

13. The method according to claim 9, wherein the composition comprises, per daily dose or per 100 ml composition:
 (a) 100-500 mg EPA,
 (b) 1000-1500 mg DHA,
 (c) 50-600 mg phospholipids,
 (d) 200-600 mg choline,
 (e) 400-800 mg uridine monophosphate,
 (f) 20-60 mg vitamin E,
 (g) 60-100 mg vitamin C,
 (h) 40-80 µg selenium,
 (i) 1-5 µg vitamin B12,
 (j) 0.5-3 mg vitamin B6, and
 (k) 200-600 µg folic acid.

14. The method according to claim 13, wherein the composition comprises, per 100 ml composition:
 (a) 200-400 mg EPA,
 (b) 1100-1300 mg DHA,
 (c) 60-200 mg phospholipids,
 (d) 300-500 mg choline,
 (e) 500-700 mg uridine monophosphate,
 (f) 30-50 mg vitamin E,
 (g) 70-90 mg vitamin C,
 (h) 50-70 µg selenium,
 (i) 2-4 µg vitamin B12,
 (j) 0.5-2 mg vitamin B6, and
 (k) 300-500 µg folic acid.

15. The method according to claim 1, wherein the composition has, per 100 ml composition, an energy content of 50-130 kcal, a protein content of 1-10 g, a lipids content of lipids 1-5 g, and a content of digestible carbohydrates of 4-20 g.

16. The method according to claim 1, wherein said subject has a mini-mental state examination (MMSE) score of 20-30.

17. The method according to claim 16, wherein said subject has a MMSE score of 20-26.

18. The method according to claim 1, wherein said subject is drug-naïve.

19. The method according to claim 1, wherein the composition is enterally administered to the patient at least one time per day for a period of at least 12 weeks.

20. The method according to claim 19, wherein the composition is enterally administered to the patient at least one time per day for a period of at least 18 weeks.

21. The method according to claim 2, wherein the recognition test is selected from RAVLT-recognition, RBANS-recognition and/or CVLT-recognition.

* * * * *